(12) United States Patent  
Taras et al.

(10) Patent No.: US 7,575,579 B2  
(45) Date of Patent: Aug. 18, 2009

(54) DRILL GUIDE TISSUE PROTECTOR

(75) Inventors: John Stanley Taras, Moorestown, NJ (US); Dennis L. Steffen, Tavernier, FL (US)

(73) Assignee: Union Surgical, LLC, Moorestown, NJ (US)

(*) Notice: Subject to any disclaimer, the term of this patent is extended or adjusted under 35 U.S.C. 154(b) by 364 days.

(21) Appl. No.: 11/009,625

(22) Filed: Nov. 18, 2004

(65) Prior Publication Data

US 2006/0106399 A1    May 18, 2006

(51) Int. Cl.
*A61B 17/17* (2006.01)
*A61B 17/90* (2006.01)
*A61B 17/58* (2006.01)

(52) U.S. Cl. ............................ 606/96; 606/104; 606/86; 600/201

(58) Field of Classification Search ................ 606/61, 606/96, 99, 205, 208, 86, 97, 104, 207, 209; 600/201–246
See application file for complete search history.

(56) References Cited

U.S. PATENT DOCUMENTS

| | | | | |
|---|---|---|---|---|
| 2,181,746 A | * | 11/1939 | Siebrandt | 606/96 |
| 2,779,224 A | * | 1/1957 | Coggburn | 81/3.44 |
| 3,744,481 A | * | 7/1973 | McDonald | 600/213 |
| 3,892,232 A | | 7/1975 | Neufeld | |
| 4,175,306 A | * | 11/1979 | Bigelow et al. | 24/507 |
| 4,312,337 A | | 1/1982 | Donohue | |
| 4,444,180 A | * | 4/1984 | Schneider et al. | 606/96 |
| 4,722,331 A | | 2/1988 | Fox | |
| 4,917,111 A | | 4/1990 | Pennig et al. | |
| 5,013,318 A | | 5/1991 | Spranza, III | |
| 5,084,022 A | * | 1/1992 | Claude | 604/164.13 |
| 5,133,715 A | * | 7/1992 | Lenzo | 606/60 |
| D335,249 S | * | 5/1993 | Hopkins | D8/52 |
| 5,255,579 A | * | 10/1993 | Fortin | 81/424 |
| 5,478,343 A | | 12/1995 | Ritter | |
| 5,697,933 A | * | 12/1997 | Gundlapalli et al. | 606/96 |
| 5,722,978 A | | 3/1998 | Jenkins, Jr. | |
| 5,725,532 A | | 3/1998 | Shoemaker | |
| 5,746,757 A | | 5/1998 | McGuire | |
| 5,785,648 A | * | 7/1998 | Min | 600/206 |
| 5,800,099 A | * | 9/1998 | Cooper | 408/1 R |
| 5,810,217 A | * | 9/1998 | Ohsugi | 223/85 |
| 5,851,207 A | | 12/1998 | Cesarone | |
| 5,895,389 A | | 4/1999 | Schenk et al. | |
| 5,896,886 A | * | 4/1999 | Wendt | 137/318 |

(Continued)

*Primary Examiner*—Eduardo C Robert
*Assistant Examiner*—Mary Hoffman
(74) *Attorney, Agent, or Firm*—Gordon & Jacobson, PC

(57) ABSTRACT

A system includes a drill guide and a gauge wire. The drill guide has two arms rotatable relative to each other about a hinge, with each arm including a split portion of a guide. When the arms are in a closed configuration, the split portions come together to form a tubular guide. Because the arms can be opened and closed about the hinge, the guide can be split and removed from over a drill bit or pin without first removing the drill bit from the bone or the drill from the drill bit or pin. Each arm also includes a semicircular form which when the arms are closed defines a gauge wire hole parallel to the guide which is sized to receive a gauge wire. The gauge wire includes depth indicia along its length which is used to indicate the length of a fixation device for use in a procedure.

12 Claims, 3 Drawing Sheets

U.S. PATENT DOCUMENTS

| | | | |
|---|---|---|---|
| 5,899,853 A | | 5/1999 | Fowler, Jr. |
| 5,931,777 A | * | 8/1999 | Sava ........................ 600/213 |
| 5,971,920 A | * | 10/1999 | Nagel ........................ 600/206 |
| 5,991,997 A | * | 11/1999 | Schley et al. ............... 29/426.5 |
| 6,007,535 A | | 12/1999 | Rayhack et al. |
| 6,010,509 A | * | 1/2000 | Delgado et al. ............... 606/88 |
| 6,015,423 A | * | 1/2000 | Andrese .................... 606/198 |
| 6,053,362 A | * | 4/2000 | Lin ............................. 222/80 |
| D424,694 S | * | 5/2000 | Tetzlaff et al. ............. D24/143 |
| 6,059,789 A | | 5/2000 | Dinger et al. |
| 6,099,547 A | * | 8/2000 | Gellman et al. ............. 606/198 |
| 6,159,217 A | * | 12/2000 | Robie et al. .................... 606/88 |
| 6,214,013 B1 | | 4/2001 | Lambrecht et al. |
| 6,306,139 B1 | | 10/2001 | Fuentes |
| 6,315,780 B1 | * | 11/2001 | Lalonde ....................... 606/86 |
| 6,332,887 B1 | | 12/2001 | Knox |
| 6,425,901 B1 | * | 7/2002 | Zhu et al. .................... 606/142 |
| 6,436,103 B1 | | 8/2002 | Suddaby |
| 6,517,582 B2 | * | 2/2003 | Willi et al. ............... 623/22.12 |
| 6,711,789 B2 | * | 3/2004 | Ping ............................ 24/505 |
| 6,725,080 B2 | * | 4/2004 | Melkent et al. ............. 600/424 |
| 7,144,378 B2 | * | 12/2006 | Arnott ....................... 600/585 |
| 2002/0072752 A1 | * | 6/2002 | Zucherman et al. ........... 606/99 |
| 2002/0077649 A1 | | 6/2002 | Lasner |
| 2002/0183595 A1 | * | 12/2002 | Rioux et al. ................ 600/223 |
| 2004/0267275 A1 | * | 12/2004 | Cournoyer et al. ............ 606/99 |

* cited by examiner

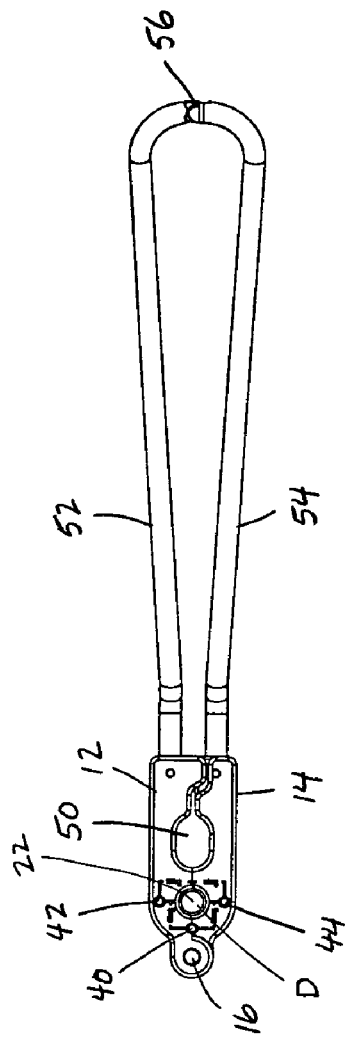
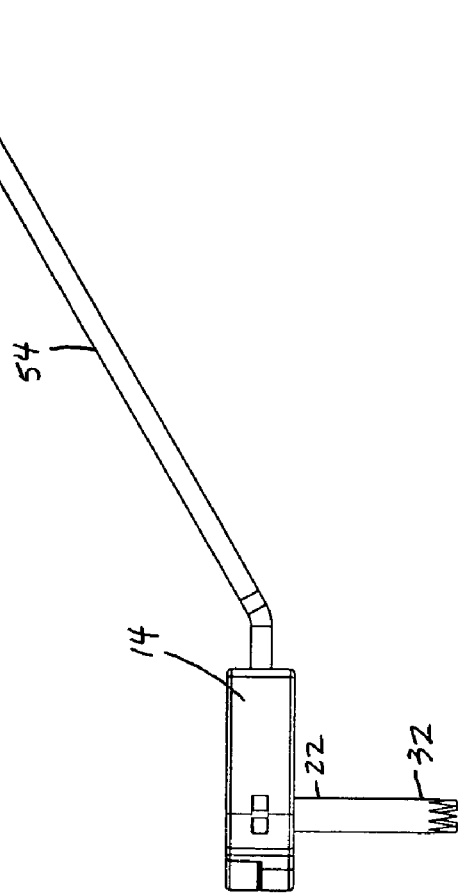
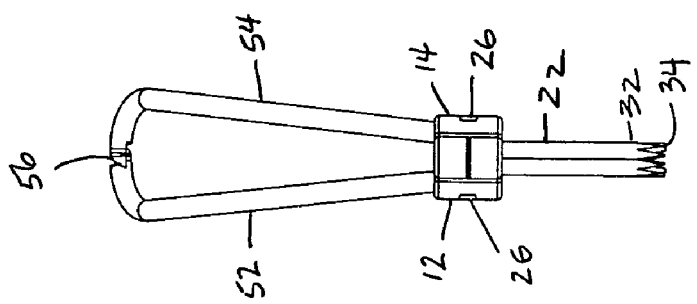

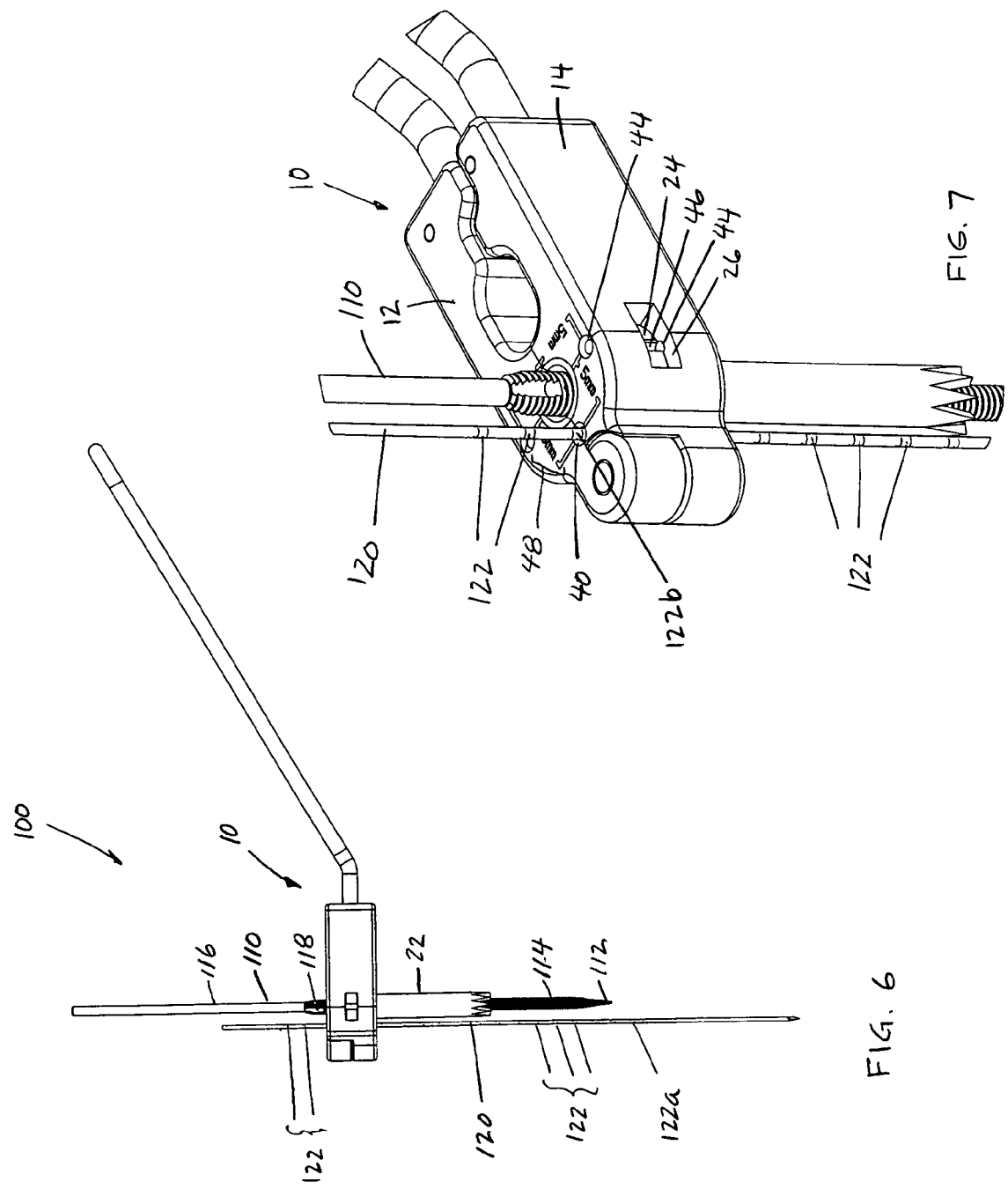

DRILL GUIDE TISSUE PROTECTOR

BACKGROUND OF THE INVENTION

1. Field of the Invention

This invention relates broadly to surgical devices. More particularly, this invention relates to orthopedic instruments, such as those used to guide pins into bone.

2. State of the Art

Numerous drill guides are known for guiding drill bits into bone. Generally a drill guide is interposed between the bone and the drill, with the guide defining a directed path along a trajectory at which the hole is to be drilled into the bone. The path is typically defined by a cannulated tube or predrilled metal block. If the hole is drilled into the bone percutaneously, the guide preferably includes a tissue protector portion which is forced through the skin and seats against the bone to create a path through which the drill bit and skin are not in contact so as not to cause destruction of the surrounding dermal tissue. If it is required to drill deeper than permitted by the interposed guide, the drill bit needs to be withdrawn from the bone and the guide, the guide is then removed, and the bit is reinserted into the partially drilled hole and the hole is drilled further. After the hole is drilled, the appropriate fixator, e.g., pin, rod, or screw, is inserted into the hole.

A drill guide is used in substantially the same way when a fixation device is self-drilling and no drill bit is used. A guide with tissue protector is provided in the correct location and orientation. The fixation device is drilled through the guide into the bone. Once the device is partially inserted along the correct trajectory the guide needs to be removed from over the fixation device to permit the fixation device to fully seated. This is typically done by releasing the fixation device from the drill, removing the guide from over the fixation device, and then reattaching the drill to drive the fixation device until fully seated in bone.

In both situations, the step of drilling or device insertion is interrupted by guide removal, complicating and extending the procedure.

SUMMARY OF THE INVENTION

It is therefore an object of the invention to provide a drill guide which can be removed from over the element it is guiding without removing the element from the drill or the bone.

It is another object of the invention to provide a drill guide which can be removed quickly and easily.

It is a further object of the invention to provide a drill guide which has a tissue protector.

It is also an object of the invention to provide a drill guide which is easy to hold by the user.

It is an additional object of the invention to provide guide adapted to be used with a depth gauge which indicates a preferred length of pin to be inserted into bone.

In accord with these objects, a system is provided which includes a drill guide having two arms rotatable relative to each other about a hinge. Each arm includes a split, preferably semi-cylindrical portion of a guide. When the arms are in a closed configuration, the split portions come together to form a tubular guide with an extending tissue protector. The distal end of the tissue protector is preferably serrated to positively engage the bone. Because the arms can be opened and closed about the hinge, the guide can be split and removed from over a drill bit or pin without first removing the drill bit from the bone or the drill from the drill bit or pin. Each arm also includes at least one semicircular form which when the arms are closed defines one or more gauge wire holes parallel to the guide which are sized to closely receive a gauge wire. A handle portion is attached to each of the arms to facilitate rotation of the arms between open and closed position. A catch may be provided to releasably lock the handles in the closed position.

The system also includes a gauge wire provided with depth indicia along its length which is used to indicate the length of a fixation device for use in a procedure in accord with the method.

In accord with a preferred method, a gauge wire is first drilled into bone adjacent the location intended for the fixation device and observed under fluoroscopy. Based upon fluoroscopic examination, if the location of the wire needs to be moved, the wire can be re-drilled without imparting serious tissue damage. Once the location of the wire is determined to be appropriate, its depth is adjusted in accord with the intended depth of the pin. With the guide in a closed configuration, the guide is fed over the gauge wire at a gauge wire hole and down the wire until the tissue protector portion enters the skin and engages the bone.

As a result of a parallel relationship between the gauge wire hole and the tubular guide, the gauge wire holds the tubular guide in the same trajectory as the gauge wire. In addition, as a result of the proximity between the gauge wire hole and tubular guide, a suitable anatomical location of the gauge wire observed under fluoroscopy infers a suitable anatomical location of the fixation device. The depth indicia on the gauge wire level with the top surface of the arms of the guide is read to determine the proper length for a fixation device for the procedure.

Once the length of the fixation device is determined, the fixation device is coupled to a drill and inserted through the closed tubular guide to the bone surface and driven. Once the fixation device is partially driven, the guide can be opened to release the pin without removing the fixation device from either the bone or the drill.

It is appreciated that at no time during the procedure is insertion of the fixation device interrupted in a manner which requires removal of a partially inserted fixation device or disengagement of the drill from the fixation device prior to inserting the fixation device into the bone the fully desired distance. Thus, the procedure is facilitated and shortened.

Additional objects and advantages of the invention will become apparent to those skilled in the art upon reference to the detailed description taken in conjunction with the provided figures.

BRIEF DESCRIPTION OF THE DRAWINGS

FIG. 3 is a top view of the drill guide tissue protector shown in a closed configuration;

FIG. 4 is a front view of the drill guide tissue protector shown in a closed configuration;

FIG. 5 is a side elevation of the drill guide tissue protector shown in a closed configuration;

FIG. 6 is a side elevation of a system of the drill guide tissue protector, a fixation pin, and a gauge wire; and FIG. 7 is a broken perspective view of the system of the drill guide tissue protector, a fixation pin, and a gauge wire.

DETAILED DESCRIPTION OF THE PREFERRED EMBODIMENTS

Figure 1:
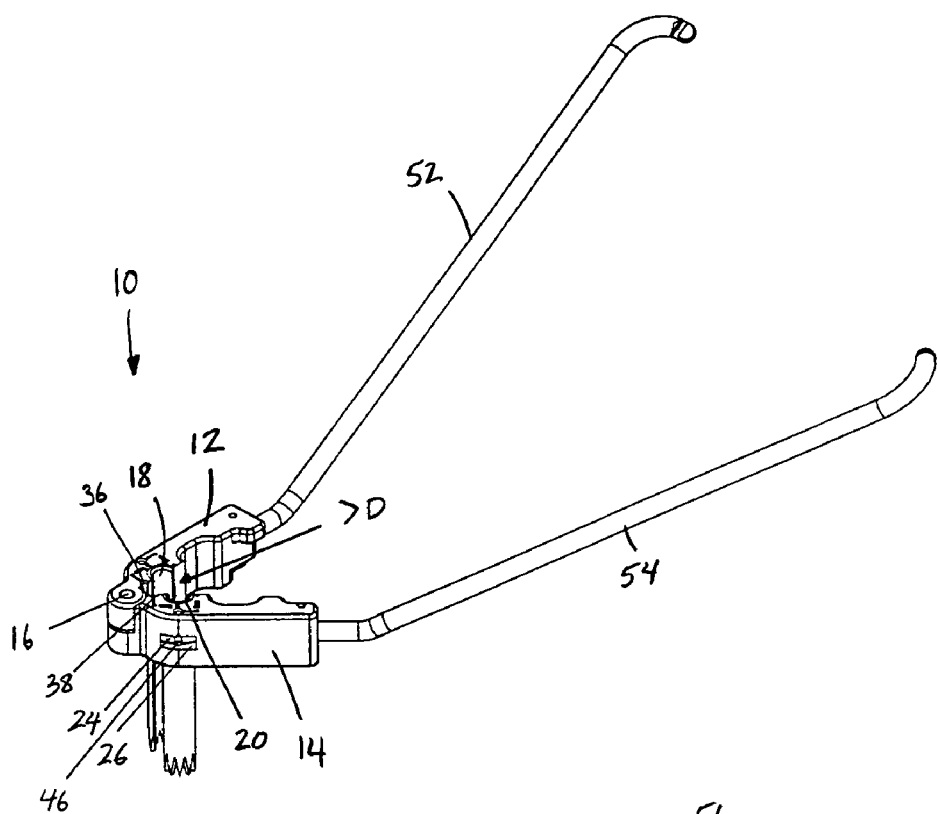
FIG. 1 is a perspective view of a drill guide tissue protector according to the invention shown in an open configuration.
Figure 2:
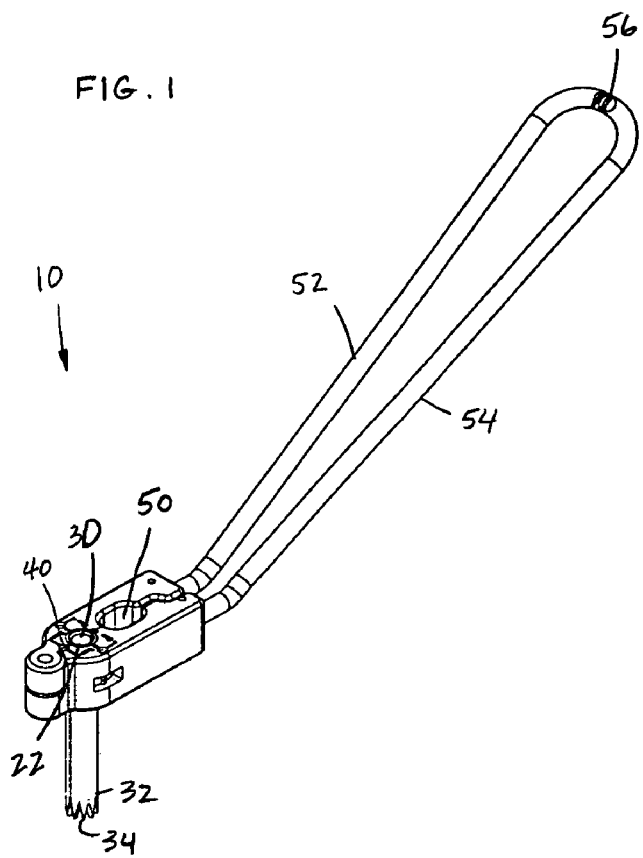
FIG. 2 is a perspective view of the drill guide tissue protector shown in a closed configuration.

Turning now to FIGS. 1-5, a drill guide 10 is shown. The drill guide has two arms 12, 14 hingedly rotatable relative to each other about a pivot pin 16. Alternatively, other hinges, including a live hinge may be used. Each arm 12, 14 is provided with a split, preferably semi-cylindrical (180°) portion 18, 20 of a tubular guide 22 having an inner diameter D. With the arms 12, 14 in an open position, the space between portions 18, 20 is at least D. Portions 18, 20 preferably include lateral tabs 24 which extend into slots 26 formed in the arms 12, 14 and operate to retain the semi-cylindrical portions of the guide 22 and also to prevent rotation of the guide within the arms.

When the arms 12, 14 are in a closed configuration, the split portions 18, 20 come together to form the tubular guide 22 of diameter D defining at its distal end a tissue protector 32. The tissue protector 32 has sufficient length to extend percutaneously to the bone surface. The end of the tissue protector 32 preferably includes serrations 34 which positively engage the bone. Because the arms 12, 14 can be opened and closed about the hinge 16, the guide 22 can be opened and removed from over a drill bit or fixation device, such as a pin 60 (see FIGS. 6 and 7 below) without first removing the pin from the bone into which it is drilled or the pin from the drill.

Each arm 12, 14 also preferably defines a semicircular channel 36, 38 extending vertically along the inner walls of the arms which when the arms are closed together define a gauge wire hole 40 parallel and distal to the guide 22 which is relatively smaller in diameter and specifically sized to closely receive a gauge wire, as discussed below. In addition, permanent gauge wire holes 42, 44 may be provided in each arm 12, 14 laterally of the guide 22. Where such laterally displaced gauge wire holes 42, 44 are provided, it may be necessary to provide a vertical channel 46 in each lateral tab 24 to permit clear passage of a gauge wire through the hole (FIG. 7). All gauge wire holes 40, 42, 44 are preferably provided equidistantly from the guide 22, and most preferably offset 5 mm from the guide, center-to-center. Markings 48 identifying the actual offset are preferably provided on the upper surface of the arms 12, 14 (FIG. 7). The arms 12, 14 preferably also define a window 50 proximal of the guide 22 to aid in viewing of the tissue protector 32 and anatomical tissue below the arms 12, 14.

A handle 52, 54 is attached to each of the arms 12, 14 to facilitate rotation of the arms between open and closed position. A catch 56 is preferably provided at the ends of the handles 52, 54 to releasably lock the handles and thus the arms in the closed position.

Referring to FIGS. 6 and 7, a system 100 including the drill guide 10, a fixation device such as a self-drilling threaded pin 110, e.g., the distraction pin described in co-owned U.S. Ser. No. 10/076,678 which is hereby incorporated by reference herein in its entirety, as well as a gauge wire 120 is shown. The pin 110 generally includes a self-drilling tip 112, a threaded portion 114, a non-threaded proximal shaft 116 which is intended to be gripped by a driver and which is removable after insertion of the threaded portion. The threaded portion includes longitudinal grooves 118 adjacent the non-threaded shaft 116 which permit rotationally driving or withdrawing the pin 110 after removing the shaft from the pin threaded portion.

The gauge wire 120 includes depth indicia 122 longitudinally displaced along its length. As discussed further below, the indicia 122 identifies the length of a pin to be used in a given bone at a given location. The indicia starts at 122a at 0 and incrementally identifies actual length from the 0 point along the wire 120. The 0 point 122a is set back from the distal end of the wire 120, because when the tip of the wire 120 is placed on the surface of the bone, 0 point 122a will be level with the top surface of the arms 12, 14 at the hole 40 to permit easy reading to the surgeon. The indicia may be etched, printed or otherwise provided onto the wire 120.

In accord with a preferred method, the gauge wire 120 is first drilled into bone adjacent the location (e.g., 5 mm offset) intended for the pin 110. The anatomical location of the gauge wire 120 can be observed under fluoroscopy. Based upon fluoroscopic examination, if the location of the wire 120 needs to be moved, the wire can be re-drilled without imparting serious tissue damage. Once the location of the wire 120 is determined to be appropriate, its depth is adjusted in accord with the intended depth of the pin 110. Then, the guide 10 is closed about or fed over the gauge wire 120 either at hole 40, 42 or 44, as selected according to a desired approach by the surgeon for insertion of the pin 110, and down the wire until the serrated edges 34 of the tissue protector portion 32 of the tubular guide 22 are entered through the skin and engage the subject bone to stabilize the guide 22. The handles 52, 54 of the guide 22 are preferably locked together at 56.

The gauge wire 120 and holes 40, 42, 44 are relatively sized such that the gauge wire is closely received in a respective gauge wire hole to hold the guide 10 at the same trajectory as the gauge wire. Preferred tolerances are 0.010 inch, defining a 0.005 inch annular ring around the gauge wire. This, in combination with the parallel relationship between the gauge wire holes 40, 42, 44 and the tubular guide 22 causes the gauge wire 110 to hold the tubular guide 22 in the same trajectory as the gauge wire. In addition, as a result of the proximity between the gauge wire hole and tubular guide, such proximity preferably being a common distance for each of the gauge wire holes relative to the tubular guide, a suitable anatomical location of the gauge wire 120 observed under fluoroscopy infers a suitable anatomical location of the pin 110. The depth indicia 122b on the gauge wire 120 which is located level or nearest level with the top surface of the arms 12, 14 of the guide 10 suggests the proper length of the pin 110 for the procedure (FIG. 7). Of course, adjustments may be made by the surgeon to choose a pin length of longer or shorter length than indicated by the indicia.

Once the length of the fixation device is determined, it is coupled to a drill and inserted through the closed tubular guide 22 to the bone surface and drilled. Once the fixation device is partially driven to the extent where it will maintain a trajectory upon removal of the guide, the handles 52, 54 of guide can be unlocked at catch 56 and the arms 12, 14 rotated to open the tubular guide 22 and release the pin 110 without removing the pin from either the bone or the drill. A retractor is then used to keep skin and other tissue from contacting the pin 110, and the pin is drilled the remaining distance into the bone. The gauge wire 120 is then removed from the bone.

It is appreciated that at no time during the procedure is insertion of the pin interrupted in a manner which requires removal of a partially inserted pin or disengagement of the drill from the pin prior to inserting the pin into the bone the fully desired distance. Thus, the procedure is facilitated and shortened.

In addition, the guide may be used to drill holes with a drill bit in a similar manner. The tissue protector is contacted against the bone and the drill bit is drilled through the tubular guide into bone. If it becomes necessary to drill a distance which requires removal of the guide 10, the guide may be opened from about the bit without removal of the bit from the drill, and the drilling procedure may then be continued. A gauge wire 120 within a gauge wire hole 40, 42, 44 may be used to maintain or suggest the trajectory of the drilled hole.

There have been described and illustrated herein an embodiment of a drill guide tissue protector and methods of using the same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A guide for guiding the insertion of a fixation device, comprising:
   a) a first element defining a first semi-cylindrical groove with a semicircular cross-section;
   b) a second element defining a second semi-cylindrical groove with a semicircular cross-section coupled relative to said first element and movable relative thereto between an open position in which a space is defined between said first and second grooves for receiving the fixation device, and a closed position in which said first and second semi-cylindrical grooves define a tubular guide parallel with the grooves for the fixation device;
   c) a first tissue protector portion extending from said first element;
   d) a second tissue protector portion extending from said second element, wherein said first and second tissue protector portions together form a tubular cylinder longitudinally extending coaxial with and on one side of said tubular guide; and
   e) first and second arm portions, said first and second elements coupled to said first and second arm portions, and said first and second arm portions rotatable about a hinge, each of said arm portions having a handle which facilitates moving said first and second arm portions between open and closed positions, each said handle having a distal portion coupled to said respective first and second arm portions and an opposite proximal portion, wherein when said proximal portions of said handles are moved toward each other, said first and second elements are moved toward said closed position and the first and second tissue protector portions are moved together into said tubular cylinder, and said first and second arm portions defining at least one circular gauge wire hole substantially smaller in diameter than said tubular guide, said at least one gauge wire hole extending parallel to said tubular guide.

2. A guide according to claim 1, wherein:
   said first and second elements are rotatable relative to a pivot axis.

3. A guide according to claim 1, wherein:
   said handles include a lock which releasably locks said arm portions in said closed position.

4. A guide according to claim 1, wherein:
   each of said first and second arm portions arms defines a portion of said at least one gauge wire hole, and together said arms arm portions define the entirety of said at least one gauge wire hole.

5. A guide according to claim 1, wherein:
   said at least one gauge wire hole defines a plurality of gauge wire holes equidistantly displaced from said tubular guide.

6. A drill and fixation device guide, comprising:
   a) a first portion defining a first inner groove extending circumferentially 180° and having a diameter of D;
   b) a second portion defining a second inner groove extending circumferentially 180° and having a diameter of D;
   c) a pivot, said first and second portions being rotatable relative to said pivot such that in an open position relative to each other a space is defined between said first and second inner grooves having an opening therebetween of at least D, and in a closed position said first and second portions define a tubular guide having a circular cross-sectional diameter of D;
   d) a first tissue protector extending from said first portion;
   e) a second tissue protector extending from said second portion, wherein said tissue first and second tissue protectors together form a tubular cylinder longitudinally extending coaxial with and on one side of said tubular guide, said first and second tissue protectors includes serrated edges at an end opposite said first and second portions;
   f) a lock for releasably locking said first and second portions in said closed position;
   g) a first handle having a distal end operably coupled to said first portion and a proximal end engageable by a user; and
   h) a second handle having a distal end operably coupled to said second portion and a proximal end engageable by the user, wherein said first and second handles facilitate moving said first and second portions between said open and closed positions, with movement of said proximal ends of said first and second handles toward each other causing said first and second portions to move toward said closed position in which said first and second portions define a tubular guide.

7. A guide according to claim 6, further comprising:
   first and second arm portions which are rotatable about said pivot, said first arm portion being positioned between said first portion and said first handle, and said second arm portion being positioned between said second portion and said second handle.

8. A guide according to claim 6, wherein:
   said lock is provided at ends of said handles.

9. A drill and fixation device guide, comprising:
   a) a first portion defining a first inner groove extending circumferentially 180° and having a diameter of D;
   b) a second portion defining a second inner groove extending circumferentially 180° and having a diameter of D;
   c) first and second arm portions each having a handle, said first portion coupled to said first arm portion and said second portion coupled to said second arm portion;
   d) a pivot, said first and second arm portions being rotatable relative to said pivot such that in an open position relative to each other a space is defined between said first and second inner grooves having an opening therebetween of at least D, and in a closed position said first and second portions define a tubular guide having a circular cross-sectional diameter of D, said handles of said first and second arm portions facilitating moving said first and second portions between the open and closed positions, wherein said arm portions define a plurality of gauge wire holes substantially smaller in diameter than D, said gauge wire holes equidistantly displaced from said tubular guide;
e) a first tissue protector extending from said first portion;
f) a second tissue protector extending from said second portion, wherein said tissue first and second tissue protectors together form a tubular cylinder longitudinally extending coaxial with and on one side of said tubular guide;
g) a lock for releasably locking said first and second portions in said closed position; and
said arm portions define a plurality of gauge wire holes equidistantly displaced from said tubular guide.

10. A guide according to claim 9, wherein:

each of said arm portions defines a portion of one of said gauge wire holes, and together said arm portions define an entirety of one of said gauge wire holes.

11. A guide according to claim 7, wherein:

said arm portions define a window proximal of said tubular guide.

12. A guide according to claim 4, wherein: said at least one gauge wire hole has an axis and a length that extend parallel to said pivot axis.

* * * * *